United States Patent

Oku

[11] Patent Number: 5,107,848
[45] Date of Patent: Apr. 28, 1992

[54] CUFF MECHANISM FOR BLOOD PRESSURE METER

[75] Inventor: Akihiko Oku, Kyoto, Japan

[73] Assignee: Omron Corporation, Kyoto, Japan

[21] Appl. No.: 533,835

[22] Filed: Jun. 6, 1990

[30] Foreign Application Priority Data

Jul. 13, 1989 [JP] Japan .................................. 1-82510[U]

[51] Int. Cl.⁵ .............................................. A61B 5/022
[52] U.S. Cl. ................................................... 128/686
[58] Field of Search ................ 128/678, 677, 686, 687

[56] References Cited

U.S. PATENT DOCUMENTS

| 2,405,265 | 8/1946 | McAlpine | 128/686 |
| 4,206,765 | 6/1980 | Huber | 128/686 |
| 4,799,492 | 1/1989 | Nelson | 128/677 |

Primary Examiner—William E. Kamm
Assistant Examiner—Scott R. Akers
Attorney, Agent, or Firm—Foley & Lardner

[57] ABSTRACT

A cuff for a blood pressure meter comprising a casing, a cylindrical collar accommodated in the casing, a slider to which one end of the collar is connected, a stopper for the slider, a knob for the slider, a spring for interconnecting the knob and slider, and an indicator for indicating when the deformation of the spring is within a certain amount of displacement.

10 Claims, 5 Drawing Sheets

CUFF MECHANISM FOR BLOOD PRESSURE METER

BACKGROUND OF THE INVENTION

1. Field of the Invention

The present invention relates generally to a cuff mechanism for blood pressure meters. More specifically, it relates to a finger cuff for an oscillometric sphygmomanometer.

The oscillometric method of determining blood pressure through detection of pulse oscillations was first reported by Roy and Adami in 1890. In the method, blood pressure is determined indirectly, as opposed to actually sticking a needle in the bloodstream, by occlusion of an artery by cuff pressurization. When cuff pressure is high enough to close an artery and thus stop the flow of blood, the pressure can be gradually released and compared to the blood flow returning to the artery. However, not until recently with the invention of computers and microprocessors has man been able to take advantage of this method.

2. Description of the Prior Art

The oscillometric method of determining blood pressure has traditionally involved mainly the optical oscillation method. In the optical oscillation method, a light emitting diode (LED) inside the cuff beams infrared light into the body. Since blood inside the artery absorbs more infrared than other living tissues, the amount of infrared that is exposed to a phototransistor (PTr) is a function of the blood volume in the artery. One disadvantage with this method is its reliance on light for measurement. Measurements conducted in daylight risk inaccuracy due to sunlight interfering with the infrared light. Another disadvantage with an optical oscillometric apparatus is that cuff construction for such a device is complicated and costly due to the infrared elements. Not only are the photoelectric devices expensive in and among themselves, but also they restrict bladder construction. The bladder construction must conform to the necessity of the photoelectric devices to be properly aligned with respect to the artery. Thus, bladders in the prior art contain many ridges which expand together in order to tighten the cuff. Although this allows the LED and the PTr to maintain proper alignment, the complex construction is more expensive and less effective than the simple bladder employed in this invention. First, the ridges reduce the accuracy of the measured blood pressure because the measurement is a function of the bladder's surface area contact with the skin. Secondly, the need for fitting all sizes of fingers necessitates a large initial diameter into which voluminous air pressure must be pumped.

SUMMARY OF THE INVENTION

To overcome the parameters imposed on cuff construction by the optical oscillation method, it is a primary object of this invention to utilize a blood pressure measuring apparatus that employs a cuff oscillation method to determine blood pressure. The cuff oscillation method measures blood pressure through tiny fluctuations in the cuff pressure. Thus, the cuff pressure itself is very important.

A major objective of this invention is to increase the contacting area of the cuff to the finger. Prior art involving the oscillation method was limited to this end by the necessity of having the LED and PTr properly aligned with the blood vessel. No such restrictions apply here. The cuff can fully encompass the bladder and finger, providing a snug fit.

Yet another object of this invention is to incorporate into the cuff a smooth inflatable bladder comprising a single piece of material. This simple design further helps to ensure an adequate fit in which the whole surface area comes in contact with the appendage.

Another object of this invention is to reduce the amount of air that must be pumped into the bladder. The less air needed to secure the finger in the cuff, the more pronounced the changes in the cuff pressure will be during measurement and, thus, the higher the accuracy of the measurement. Therefore, the cuff is initially compressed around the finger manually by pulling the cuff down a slide track. The construction of such a device is in its simplicity which is less expensive than the automated pumping used in the prior art and additionally provides for more accurate results in a cuff oscillation sphygmomanometer.

As, in this embodiment, the left index finger is to be cuffed, it is a further object of the invention to provide a cuff that is adaptable to fit all sizes of fingers. The means for tightening the cuff is provided by a slider attached to one end of the cuff. The patient himself can obtain sufficient cuff pressure by inserting his finger into the cuff and pushing the slider down a slide track. In this embodiment, a marker can be observed informing the patient that an adequate cuff pressure threshold for proper blood pressure measurement has been reached.

Still another object of this invention is to allow the patient some leeway in obtaining the adequate cuff pressure threshold. This will help to ensure proper blood pressure measurement, reduce the probability of the patient failing to secure the proper cuff pressure, and eliminate any anxiety the patient may have regarding his ability to correctly operate the apparatus. Therefore, adequate cuff pressure for measurement is already provided when the marker starts to appear. The patient can continue to tighten the cuff until the marker is fully revealed and even tighten further without adversely affecting the measurement.

As demonstrated, a primary object of this invention is to provide a simpler and less expensive cuff. To this end, the cuff oscillation method provides a means for determining blood pressure without employing optical elements such as a light-emitting diode or a phototransistor. The cuff oscillation method, in fact, simply determines arterial volume change by tiny fluctuations in cuff pressure. These fluctuations result from the rise and fall of the blood pressure during the heart cycle. The artery opens when the cuff pressure becomes lower than the blood pressure generated by the beating of the heart. However, the blood pressure, constantly changing between the systolic and diastolic pressures, rises above and falls below the gradually declining cuff pressure until the cuff pressure finally becomes lower than the diastolic blood pressure. The relationship between the opening of the blood vessel and the cuff pressure is called the volumetric change and a volumetric pulse wave can be determined. Further, this pulse wave increases for a period of time, reaches a maximum, and then decreases until the cuff pressure is finally less than the diastolic pressure. When graphed with respect to time and pressure, the amplitudes of the volumetric pulse wave visually represent what is called an envelope of oscillation. Blood pressure is determined by using this envelope curve, which represents tiny fluctuations in the cuff pressure.

Other objects and advantages of this invention will become apparent from the following description and accompanying drawings.

BRIEF DESCRIPTION OF THE DRAWINGS

FIG. (1) is a cross-sectional view of the casing, cuff, and sliding mechanism.

FIG. (2A) is a cross-sectional view of a sliding mechanism before cuff pressurization operation.

Figure 1:
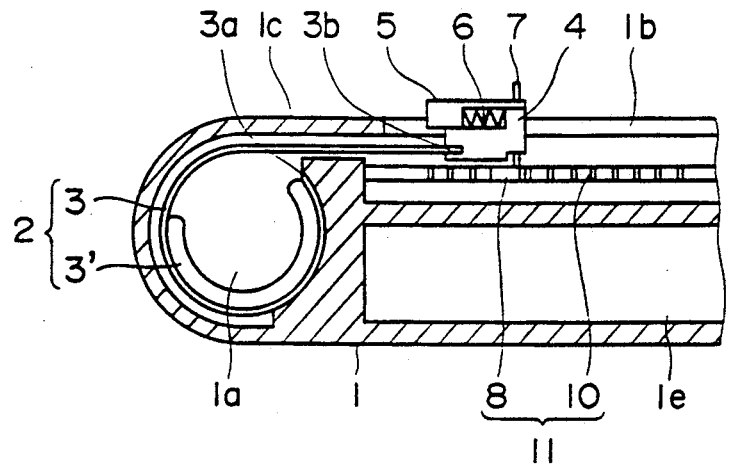

FIG. (2B) is a top view of a knob of the slider before cuff pressurization operation.

FIG. (3A) is a cross-sectional view of the slider after the cuff pressurization operation.

FIG. (3B) is a top view of the knob after the cuff pressurization operation.

FIG. (4) is a bottom view of a fixing mechanism for the slider.

FIG. (5) depicts a block diagram of the blood pressure meter for which the cuff mechanism was designed.

FIG. (6) represents a flow chart showing an operation of a blood pressure meter depicted in FIG. (5).

FIG. (7) depicts an envelope curve used to determine maximum amplitude of pulse, systolic pressure, and diastolic pressure.

DETAILED DESCRIPTION OF THE EMBODIMENTS

Referring to FIG. (1), 1 is a casing for the cuff apparatus which, in this embodiment, is made of plastic. A cuff 2 consists of two parts, an inflatable bladder 3' and a collar 3. One end of a collar 3a is fixedly attached to the casing 1 and another end 3b extends into a slider 4. The bladder 3' is attached to the inside of the collar 3 and forms a circle around a space 1a in order to secure the finger when the slider 4 is pulled down a slide track 1b. Furthermore, the slide track 1b is embedded in a top casing 1c. In one embodiment numbers (i.e. 1,2,3,4,5) may be printed on the top casing 1c next to the slide track 1b indicating cuff size.

Referring to FIG. (2A), a knob 5 is provided above the slider 4 and protruding above the top casing 1c. In this embodiment, a marker 4a is situated on top of slider 4 and a window 5a is placed in knob 5. As the knob 5 is pulled down the slide track 1b, see FIG. (3A), the marker 4a can be viewed through window 5a, see FIG. (3B), indicating when proper cuff pressure is attained. However, in another embodiment, the window can be eliminated and the knob can be shortened to enable it to slide completely past the marker.

Again referring to FIG. (2A), slider section 4 is interconnected to knob 5 by an elastic or biasing means 6. In this embodiment, the elastic means 6 is a prestressed spring in which deformation of the elastic means 6 occurs when the cuff pressure is adequate for measuring blood pressure. Besides a spring, other elastic means may be used such as: a coil, a weight-loaded regulator, or some kind of elastic rubber like polyurethane. Means for securing the sliding mechanism is provided for in this embodiment by a pin 7 with a button 7a on top and a coil spring 9 on the bottom section 7b which fits into a mechanism 11 for fixing the slider. As shown in FIG. (2B), the pin 7 is independent from knob 5 as a space 5b has been provided in the knob to accommodate the pin. Also, the slider has a small vertical space 4b to accommodate the movement of the pin. Referring to FIG. (4), a fixing mechanism 11 consists of a hook 8 mounted upon the bottom of the pin 7b and parallel to a grooved track 10. As the slider's knob 5 is pulled to secure the finger in the cuff 2, the hook 8 correspondingly moves down the grooved track 10. Each step of the way, hook tips 8a lodge into teeth 10a of the track, inhibiting backward movement of the slider 4 which now is effectively secured by the pin 7. The grooved track 10 should be located in the middle of the casing 1 to allow room for blood pressure meter circuits stored in such casing space 1e.

Referring to Figs. (5) and (6), once the finger has been properly secured in the bladder 3', the patient can start measuring his blood pressure by pushing start button 1D. When the start button 1D is pushed, a pump 12 begins to pump air through an air duct 13 (ST 1). At this point, a pressure sensor 14 provides data corresponding to the value of pressure in bladder 3' for a micro processing unit (MPU) 15 to judge if a target of pressure has been reached (ST 2). If the MPU 15 judges no, the target pressure has not been reached, then the pump 12 will continue pumping and the pressure sensor 14 will further provide data corresponding to the increasing value of pressure in bladder 3' for the MPU 15 (ST 2). If the MPU 15 judges that the target pressure has been reached, then the pump will stop pressuring (ST 3). Next, the MPU 15 performs the function of detecting a short of pressuring in the bladder 3', detecting whether or not the cuff pressure is sufficient for blood pressure measurement (ST 4). The MPU 15 then judges whether the bladder 3' is short of pressure (ST 5). If the MPU 15 judges yes there is a shortage of pressure, then it changes the target pressure (ST 6) and begins again at ST 1. If, on the other hand, no shortage of pressure is detected, then a slow release valve 16 is initiated (ST 7). Incidentally, in this embodiment, the slow release valve 16 releases about 2-6 mmHg/sec. During this time, the pressure sensor 14 measures the pressure in the bladder 3', and the MPU 15 performs the function of measuring the systolic and diastolic blood pressures (ST 8).

Figure 2A:
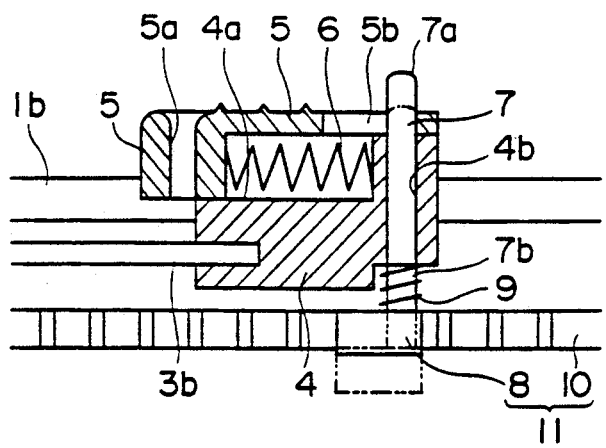
Figure 2B:
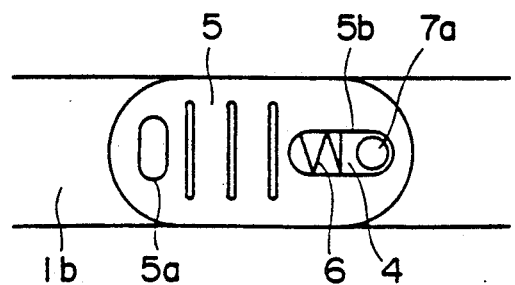
Figure 3A:
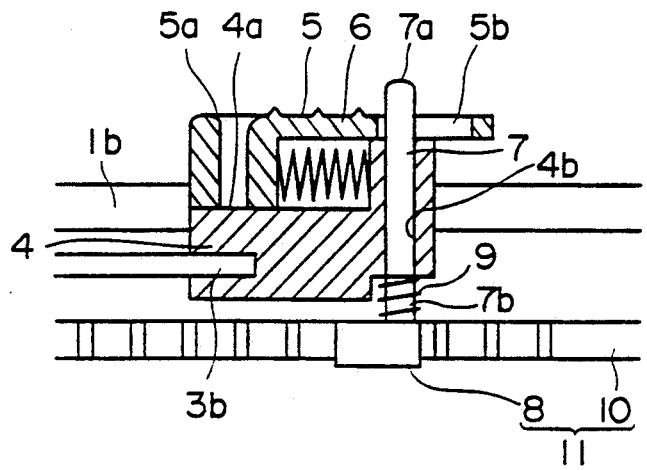
Figure 3B:
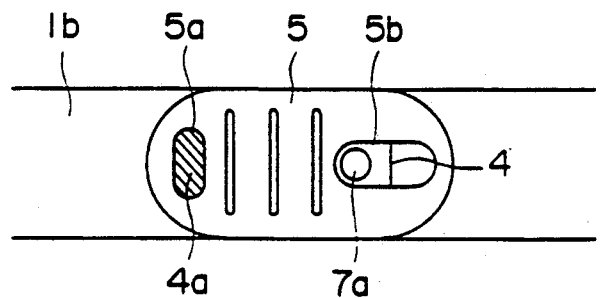
Figure 4:
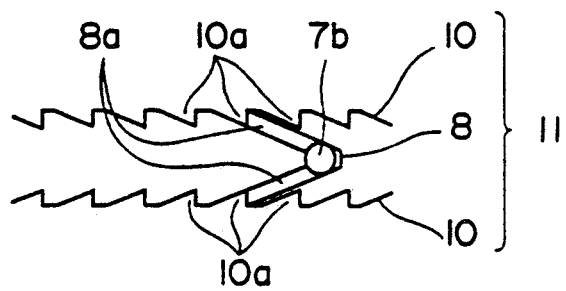
Figure 5:
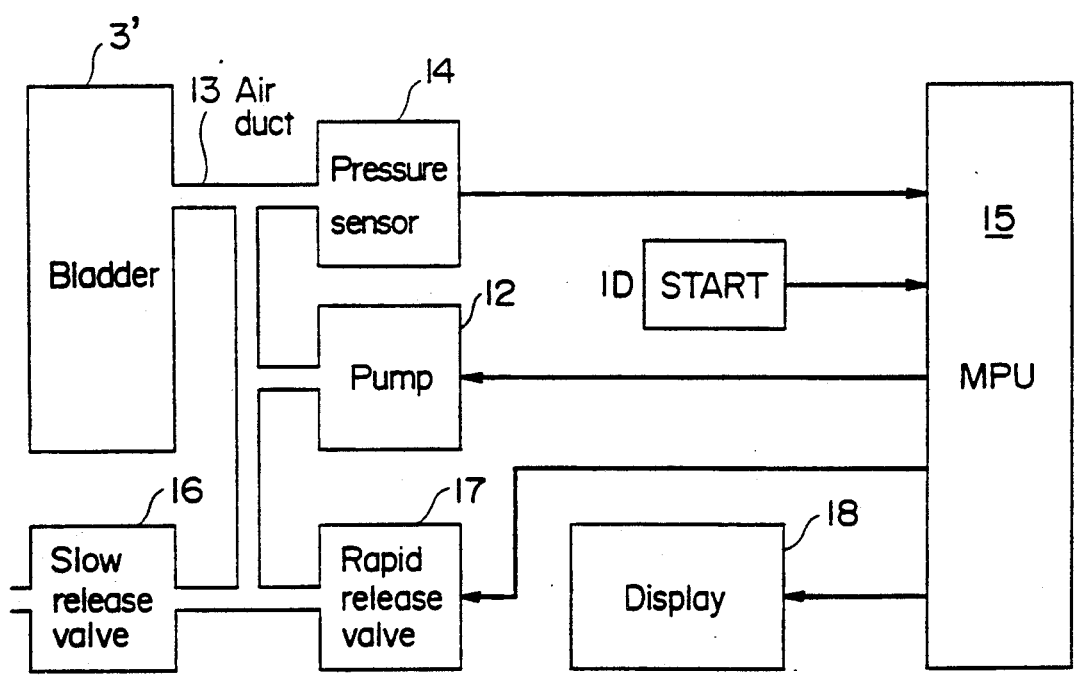
Figure 6:
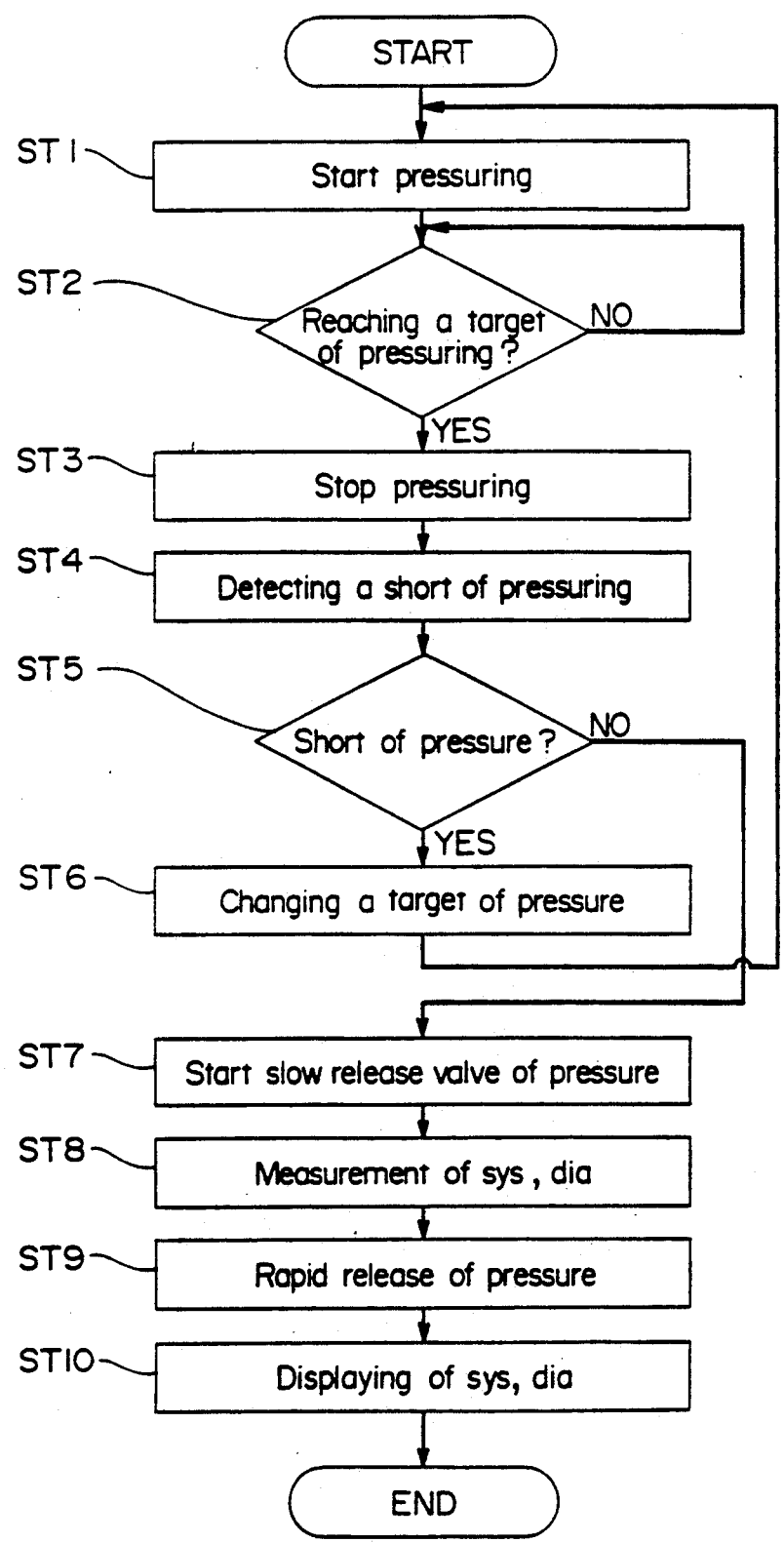
Figure 7:
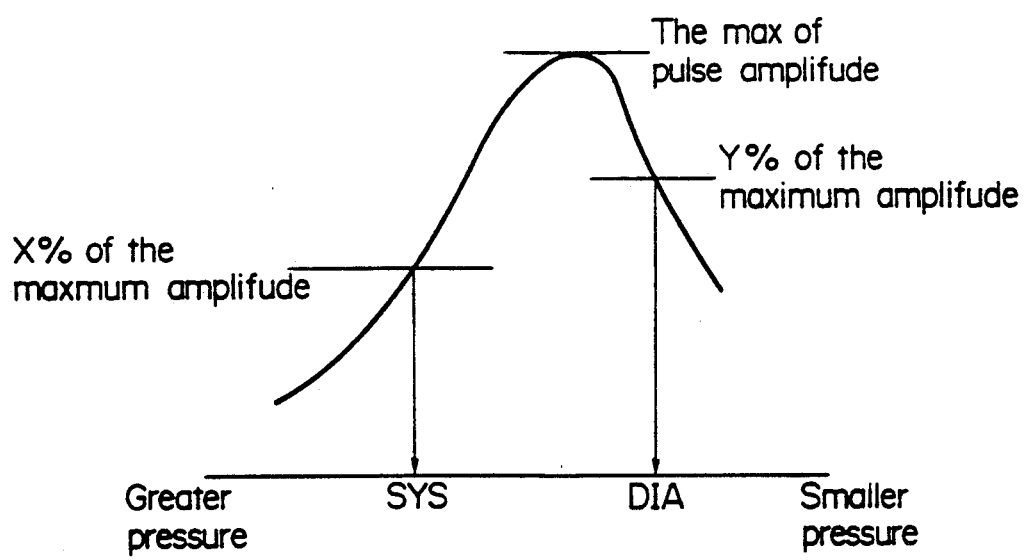

Referring to FIG. (7), the MPU 15 utilizes an envelope curve of the type described in the "Summary of the Invention" to determine the systolic and diastolic blood pressures. First, the MPU 15 determines the maximum amplitude of the pulse (MAP). Secondly, the MPU 15 calculates x% of the maximum amplitude of pulse and determines the cuff pressure at which x% of the MAP occurs. This cuff pressure is the systolic blood pressure and occurs at the onset of the tiny fluctuations in the cuff pressure. Similarly, the MPU 15 then calculates y% of the MAP and the corresponding cuff pressure. This is the diastolic blood pressure and occurs at the end of the fluctuations in the cuff pressure. When the MPU 15 has measured the systolic and diastolic pressures, the rapid release valve 17 is activated to rapidly release the cuff pressure (ST 9). Finally, the systolic and diastolic blood pressures are displayed on a display 18 (ST 10). At this point, the patient pushes the pin button 7a which, in turn, disengages the hook 8 from the track 10 (as shown in FIG. 2A), effectively releasing the slider 4 to return to its original position with the collar 3.

The above description and accompanying drawings are merely illustrative of the applications of the principles of the present invention and are not limiting. Many other embodiments falling under the spirit and scope of this invention may be devised by those skilled in the art. Accordingly, this invention is only limited by the scope of the appended claims.

What is claimed is:

1. A cuff mechanism for a blood pressure meter, comprising:
   a) a casing;
   b) a collar having a pair of ends in said casing, one end of said collar being connected to said casing;
   c) a slider movable in said casing, the other end of said collar being connected to said slider;
   d) means for sliding said slider in said casing;
   e) a knob positioned on said slider and movable therewith;
   f) means for biasing said slider relative to said knob; and
   g) marker means for indicating the displacement of said biasing means whereby a proper cuff is attained.

2. The cuff of claim 1, including an inflatable bladder positioned in said collar.

3. The cuff of claim 1, wherein said marker means includes a mark on a top surface of said slider and a window in said knob cooperating with said mark.

4. The cuff of claim 1, wherein said marker means includes a mark on a top surface of said slider and is visible when said knob moves a predetermined distance so as to expose said mark.

5. The cuff of claim 1, including means for adjustably fixing said knob, and said slider in said casing.

6. The cuff of claim 5, further comprising a track in said casing, wherein said means for adjustably fixing cooperates with said track.

7. The cuff of claim 6, wherein said means for adjustably fixing includes a pin in said knob, and a hook on said pin, and wherein said track includes a plurality of grooves, and said hook cooperates with said grooves.

8. The cuff of claim 7, further comprising spring means for engaging said hook into cooperation with said track, said spring means for engaging being located between said hook and said pin.

9. A method of measuring blood pressure comprising:
   b) at least partially surrounding a user's finger with a cuff including a collar and a bladder,
   c) moving a slider connected to the collar to secure the finger therein,
   d) indicating to the user an adequate cuff pressure threshold,
   e) inflating the bladder with air,
   f) releasing air from the bladder and ascertaining the systolic and diastolic pressures.

10. The method of claim 9, including connecting a micro processing unit to a pump performing the inflating step and controlling the releasing step.

* * * * *